United States Patent
Skarsgard (10) Patent No.: US 10,531,956 B2
(45) Date of Patent: Jan. 14, 2020

(54) APPARATUS FOR REPAIRING HEART VALVES AND METHOD OF USE THEREOF

(71) Applicant: Peter Lloyd Skarsgard, Vancouver (CA)

(72) Inventor: Peter Lloyd Skarsgard, Vancouver (CA)

(73) Assignee: Vesalous Cardiovascular Inc., Vancouver (CA)

( * ) Notice: Subject to any disclaimer, the term of this patent is extended or adjusted under 35 U.S.C. 154(b) by 271 days.

(21) Appl. No.: 15/254,835

(22) Filed: Sep. 1, 2016

(65) Prior Publication Data
US 2017/0065418 A1   Mar. 9, 2017

Related U.S. Application Data

(60) Provisional application No. 62/214,075, filed on Sep. 3, 2015.

(51) Int. Cl.
*A61F 2/24* (2006.01)
(52) U.S. Cl.
CPC .......... *A61F 2/2487* (2013.01); *A61F 2/2436* (2013.01); *A61F 2220/0016* (2013.01)
(58) Field of Classification Search
CPC ...... A61B 17/0057; A61B 2017/00575; A61B 2017/00592; A61B 2017/00597; A61B 2017/00615; A61B 2017/00619; A61B 2017/00623; A61F 2/2487; A61F 2/2418; A61F 2/2436; A61F 2/2454; A61F 2/2457; A61F 2250/0004; A61F 2250/001; A61F 2250/0012; A61F 2220/0016
See application file for complete search history.

(56) References Cited

U.S. PATENT DOCUMENTS

| 8,845,717 | B2 | 9/2014 | Khairkhahan et al. |
| 8,870,950 | B2 | 10/2014 | Hacohen |
| 2007/0239272 | A1* | 10/2007 | Navia ............... A61F 2/2445 623/2.36 |
| 2009/0182355 | A1* | 7/2009 | Levine ............... A61F 5/0076 606/153 |

(Continued)

FOREIGN PATENT DOCUMENTS

| WO | 2007009609 A1 | 1/2007 |
| WO | 2014039392 A1 | 3/2014 |
| WO | 2014144937 A2 | 9/2014 |

*Primary Examiner* — Melanie R Tyson
(74) *Attorney, Agent, or Firm* — Oyen Wiggs Green & Mutala LLP (57) ABSTRACT

An apparatus for repairing a heart valve and methods of use thereof are provided. The apparatus includes a radially expandable body and a blood-permeable member attached to the body at a first end and having at least one cord at a second end. The length or tension of the at least one cord is adjustable when the apparatus is implanted in a heart such that that the extent of atrial displacement of the heart's mitral leaflets during ventricular contraction can be adjusted. To implant the apparatus in a heart, the apparatus is inserted into a retaining sheath and the retaining sheath is then inserted into the heart. The retaining sheath is retracted from the apparatus and the apparatus is positioned inside the heart. The length or tension of the at least one cord is adjusted to adjust the extent of atrial displacement of the heart's mitral leaflets during ventricular contraction.

18 Claims, 12 Drawing Sheets

(56) References Cited

U.S. PATENT DOCUMENTS

| | | | |
|---|---|---|---|
| 2010/0036479 A1* | 2/2010 | Hill | A61F 2/2418 623/1.15 |
| 2010/0217382 A1 | 8/2010 | Chau et al. | |
| 2011/0208298 A1 | 8/2011 | Tuval et al. | |
| 2011/0224784 A1 | 9/2011 | Quinn | |
| 2011/0264206 A1 | 10/2011 | Tabor | |
| 2012/0197388 A1* | 8/2012 | Khairkhahan | A61F 2/246 623/2.11 |
| 2014/0121763 A1* | 5/2014 | Duffy | A61B 17/0401 623/2.11 |
| 2014/0222142 A1 | 8/2014 | Kovalsky et al. | |
| 2014/0228946 A1 | 8/2014 | Chau et al. | |
| 2014/0358223 A1* | 12/2014 | Rafiee | A61F 2/2418 623/2.13 |
| 2015/0119981 A1* | 4/2015 | Khairkhahan | A61F 2/2442 623/2.36 |

* cited by examiner

APPARATUS FOR REPAIRING HEART VALVES AND METHOD OF USE THEREOF

REFERENCE TO RELATED APPLICATIONS

This application claims priority from U.S. Patent Application Ser. No. 62/214,075, entitled APPARATUS FOR REPAIRING HEART VALVES AND METHODS OF USE THEREOF, filed Sep. 3, 2015 which is hereby incorporated herein by this reference in its entirety for all purposes. For purposes of the United States of America this application claims the benefit of U.S. Patent Application Ser. No. 62/214,075, entitled APPARATUS FOR REPAIRING HEART VALVES AND METHODS OF USE THEREOF, filed Sep. 3, 2015.

TECHNICAL FIELD

The present invention relates to apparatus for repairing heart valves and methods of use thereof. In particular, the present invention relates to apparatus for repairing mitral valves and methods of use thereof.

BACKGROUND

Conditions affecting the normal functioning of the mitral valve include, for example, mitral valve regurgitation, mitral valve prolapse, and mitral valve stenosis. Mitral valve regurgitation refers to the condition whereby the leaflets of the mitral valve fail to coapt into apposition during ventricular contraction, resulting in abnormal leaking of blood from the left ventricle into the left atrium. Mitral valve prolapse refers to the condition where the mitral leaflets bulge abnormally up into the left atrium causing irregular behavior of the mitral valve. A number of factors may affect the normal functioning of the mitral valve leaflets. For example, a stretch or tear in the chordae tendinae may prevent coaptation between mitral leaflets.

Although intermediate grades of impaired functioning of the mitral valve may not require treatment, severely impaired mitral valve function may result in symptoms (for example, breathlessness, fatigue, exercise intolerance), and may represent a threat to life expectancy. Often, invasive surgery must be performed to repair or replace an abnormal mitral valve.

Traditional mitral valve repair is an open heart procedure to correct excessive leaflet motion during ventricular contraction by either removing a diseased segment of the leaflet, or by replacing elongated or ruptured chordae tendinae with native tissue or artificial material. Open heart procedures present patients with morbidity and mortality risks and require a post-op period of convalescence that is typically several months in duration. Open heart surgery may pose prohibitive risks, or may otherwise not be ideal for some patients, including some elderly patients and patients with other health issues. Repairing the mitral valve without invasive open heart procedures may be attractive therapy for such patients.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

The present invention relates to apparatus for restoring mitral valvular competence, by correcting mitral valve prolapse, without open heart surgery. The apparatus includes a radially expandable body for implanting the apparatus in the heart of a patient without the need for open heart procedures. To fit the apparatus to the patient's heart, the apparatus includes at least one cord. The length or tension of the at least one cord may be adjusted when the apparatus is implanted in the heart to adjust the extent of atrial displacement of the mitral leaflets during ventricular contraction.

The present invention has a number of aspects. One aspect of the present invention provides an apparatus for repairing a heart valve. The apparatus includes a radially expandable body and a blood-permeable member. The blood-permeable member is attached to the body at a first end and has at least one cord at a second end opposed to the first end.

In some embodiments, the length or tension of the at least one cord is adjustable when the apparatus is implanted in a heart such that the extent of atrial displacement of the heart's mitral leaflets during ventricular contraction can be adjusted.

In some embodiments, the apparatus includes an encircling member connectable to the body for radially compressing and/or radially expanding the body.

In some embodiments, the body includes a plurality of peaks and a plurality of troughs, the peaks and troughs defined along the length of the body.

In some embodiments, the body includes a plurality of ring members, each ring member positioned on a corresponding trough.

In some embodiments, the encircling member passes through the plurality of ring members.

In some embodiments, the body is C-shaped.

In some embodiments, the blood-permeable member is an anterior blood-permeable member attached to an anterior end of the body and/or a posterior blood-permeable member attached to a posterior end of the body.

In some embodiments, the blood-permeable member is configured to extend from an atrial wall and a mitral annulus to a ventricular apex or a ventricular myocardium of the heart when the apparatus is implanted in the heart.

In some embodiments, the blood-permeable member is configured to cover an anterior mitral leaflet of the heart when the apparatus is implanted in the heart and/or to cover a posterior mitral leaflet of the heart when the apparatus is implanted in the heart.

In some embodiments, the body comprises at least one fastener for securing the body to the atrial wall of the heart when the apparatus is implanted in the heart.

In some embodiments, the at least one fastener is positioned at one or more of a first end of the body and a second end of the body.

In some embodiments, each fastener comprises at least one barb or hook.

In some embodiments, each fastener comprises a material having tissue ingrowth qualities.

In some embodiments, the apparatus includes a retaining sheath. The retaining sheath houses the body and blood-permeable member when the body is radially compressed.

In some embodiments, the retaining sheath includes one or more of an encircling member sheath, an inner sheath, and an outer sheath for staged deployment of the apparatus inside the heart.

Another aspect of the present invention provides a kit for repairing a heart valve. The kit includes an apparatus having a radially expandable body, a blood-permeable member configured to cover a mitral leaflet of a heart when the apparatus is implanted in the heart, and at least one cord for adjusting the extent of atrial displacement of the mitral leaflet during ventricular contraction when the apparatus is implanted in the heart. The kit further includes a retaining sheath for implanting the apparatus inside a heart.

In some embodiments, the kit includes a guide wire for guiding the apparatus and the retaining sheath into the heart.

Another aspect of the present invention provides a method of repairing a heart valve using an apparatus comprising a radially expandable body and a blood-permeable member attached to the body at a first end and having at least one cord at a second end opposed to the first end. The method includes inserting the apparatus inside a retaining sheath and inserting the retaining sheath containing the apparatus into the heart. The retaining sheath is retracted from the apparatus and the apparatus is positioned inside the heart. The retaining sheath is withdrawn from the heart and the length or tension of the at least one cord of the apparatus is adjusted to adjust the extent of atrial displacement of the heart's mitral leaflets during ventricular contraction.

In some embodiments, inserting the retaining sheath containing the apparatus into the heart includes inserting the retaining sheath and apparatus through the left ventricular apex or the left ventricular myocardium of the heart across the mitral valve and into the left atrium. In some embodiments, the retaining sheath and apparatus are inserted into the heart using a transcatheter approach.

In some embodiments, retracting the retaining sheath from the apparatus includes partially retracting the retaining sheath from the apparatus to release the body of the apparatus from the retaining sheath, positioning the body of the apparatus inside the heart, and further retracting the retaining sheath from the apparatus to release a blood-permeable member of the apparatus from the retaining sheath.

In some embodiments, partially retracting the retaining sheath from the apparatus releases a portion of the blood-permeable member, the anterior blood-permeable member, and/or the posterior blood-permeable member.

In some embodiments, positioning the body of the apparatus inside the heart includes rotating the apparatus such that the anterior end of the body faces the anterior mitral leaflet of the heart. In some embodiments, positioning the body of the apparatus includes releasing tension from the encircling member to radially expand the body.

In some embodiments, positioning the apparatus inside the heart includes releasing tension from the encircling member to radially expand the body. In some embodiments, positioning the apparatus inside the heart includes rotating the apparatus such that the blood-permeable member covers an anterior mitral leaflet and/or a posterior mitral leaflet of the heart. In some embodiments, positioning the apparatus inside the heart includes rotating the apparatus such that the anterior blood-permeable member covers the anterior mitral leaflet of the heart. In some embodiments, positioning the apparatus inside the heart includes rotating the apparatus such that the posterior blood-permeable member covers the posterior mitral leaflet of the heart.

In some embodiments, positioning the apparatus inside the heart further includes tensioning the encircling member of the body to reposition the apparatus inside the heart.

In some embodiments, the method further includes inserting a first end of a guide wire through the left ventricular myocardium of the heart, across the mitral valve, and into the left atrium and inserting a second end of the guide wire through the retaining sheath containing the apparatus prior to inserting the retaining sheath containing the apparatus into the heart.

In some embodiments, the method further includes withdrawing the guide wire from the heart.

In some embodiments, the method further includes securing the body of the apparatus to a left atrial wall.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Unless context dictates otherwise, the term anterior (as used herein in relation to a patient's body and parts thereof) refers to a position that is more near the front surface of the patient's body or part thereof than the rear surface of the patient's body or part thereof.

Unless context dictates otherwise, the term posterior (as used herein in relation to a patient's body and parts thereof) refers to a position that is more near the rear surface of the patient's body or part thereof than the front surface of the patient's body or part thereof.

Figure 1:
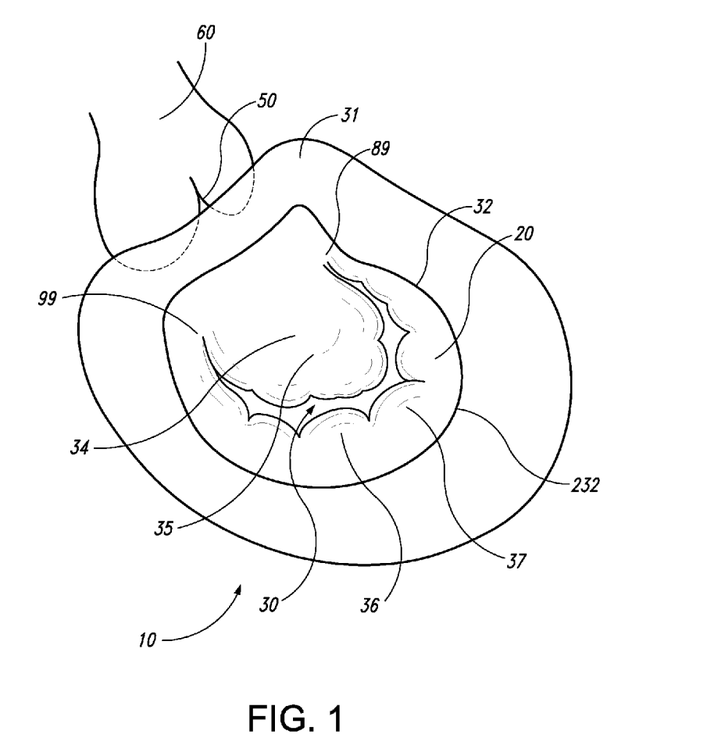
FIG. 1 is a top cross-sectional view of a heart showing normal coaptation of a mitral valve.
Figure 2:
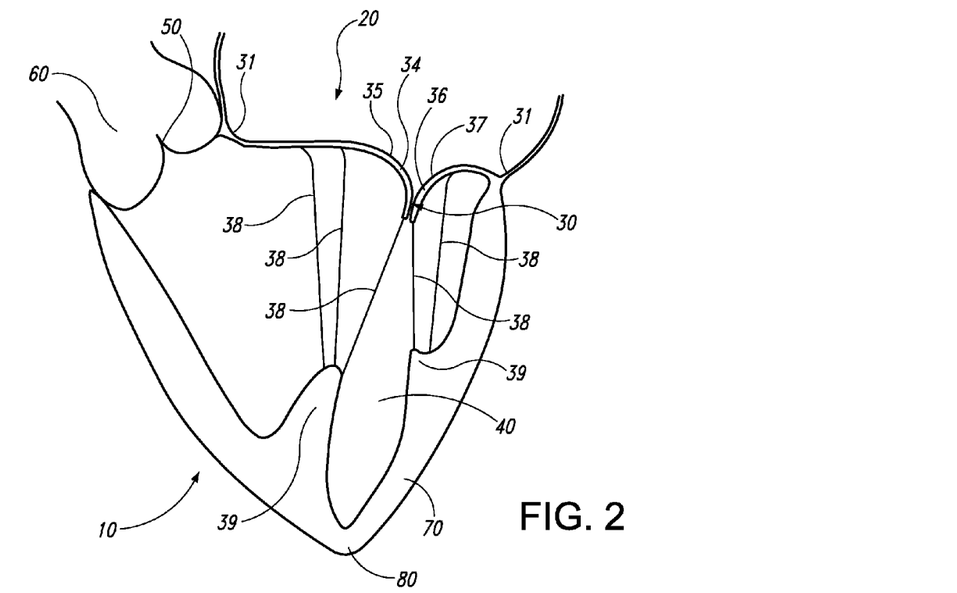
FIG. 2 is a side elevation cross-sectional view of the heart shown in FIG. 1.

The human heart 10, shown in FIGS. 1 and 2, is a muscle pump which relies on heart valves to achieve forward blood flow. In normal physiology, oxygenated blood returning from the lungs is collected in a left atrium 20, and then passes through a mitral (inlet) valve 30 to enter a left ventricle 40 (i.e. the pumping chamber). With contraction of left ventricle 40, the elevation of left ventricular pressure causes mitral valve 30 to close, preventing reversal of blood flow back into atrium 20. As ventricular pressure exceeds aortic pressure, aortic (outlet) valve 50 opens, and blood is pumped forward into aorta 60. When left ventricle 40 relaxes, the ventricular pressure drops, mitral valve 30 reopens to permit flow of blood from left atrium 20 to left ventricle 40, and the process repeats.

Mitral valve 30 separates left atrium 20 from left ventricle 40, and is comprised of a mitral annulus 32, leaflets (anterior 34 and posterior 36), chordae tendinae 38, and papillary muscles 39. During ventricular contraction (systole), the ventricular pressure rises, which forces displacement of mitral leaflets 34, 36 towards atrium 20 (i.e. commonly known as atrial or leaflet displacement). The length and integrity of chordae tendinae 38 determines the degree of leaflet displacement. In normal physiology, equal displacement of anterior mitral leaflet 34 and posterior mitral leaflet 36 results in contact (coaptation) between the leaflets, and consequent competence of mitral valve 30 (FIGS. 1 and 2).

Figure 3:
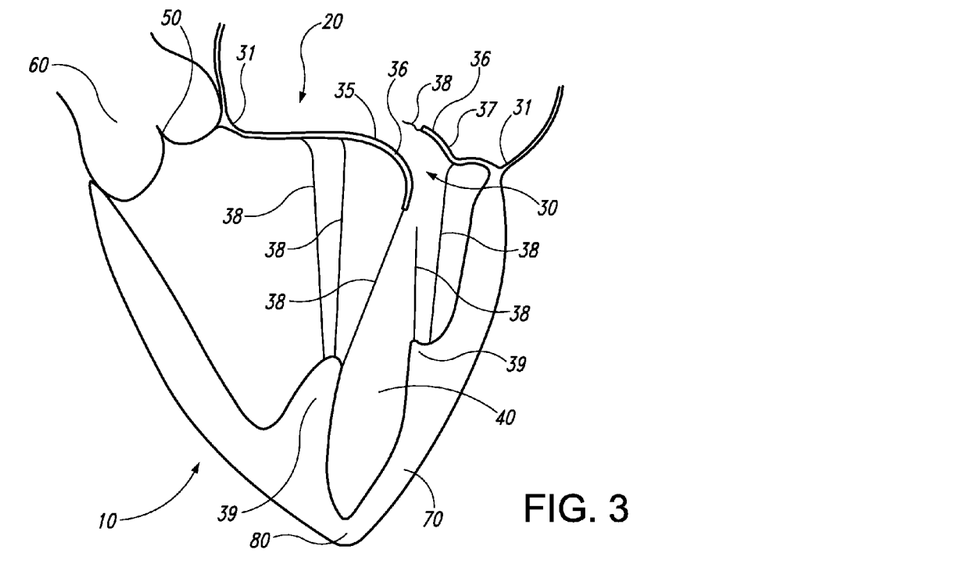
FIG. 3 is a side elevation cross-sectional view of a heart showing prolapse of a posterior mitral leaflet.

In circumstances where mitral leaflet 34 and/or 36 is supported by chordae tendinae 38 which are elongated or ruptured, ventricular contraction may result in excessive atrial displacement of the leaflet(s), and this may prevent coaptation between the leaflets (FIG. 3). This is referred to as mitral leaflet prolapse. In this circumstance, the competency of mitral valve 30 may be compromised and leakage may occur. Leakage through the mitral valve is referred to as mitral regurgitation, described elsewhere herein.

Figure 4:
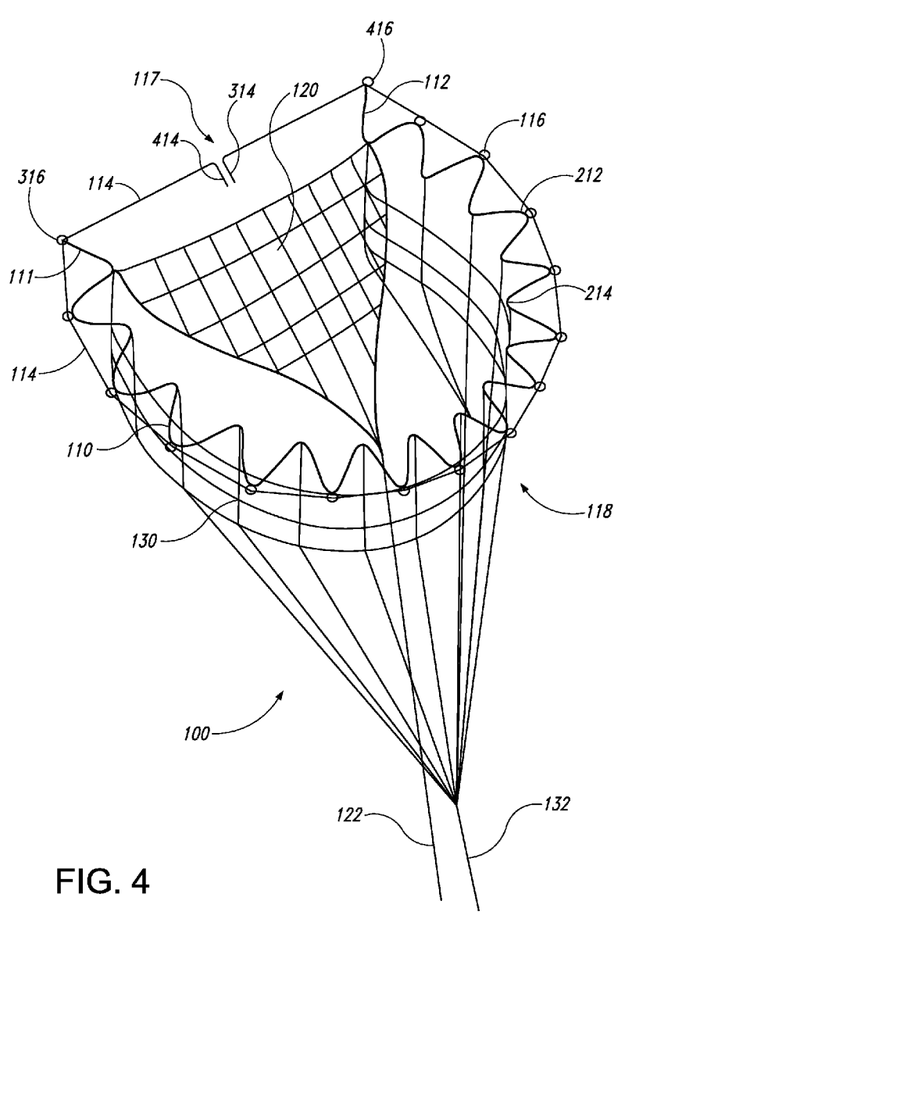
FIG. 4 is a perspective view of an apparatus for repairing a mitral valve according to an example embodiment of the present invention.
Figure 5:
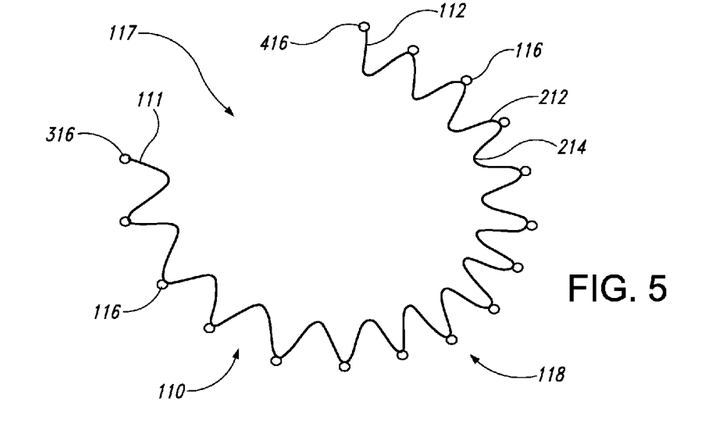
FIG. 5 is a top view of a body of the apparatus shown in FIG. 4.
Figure 6:
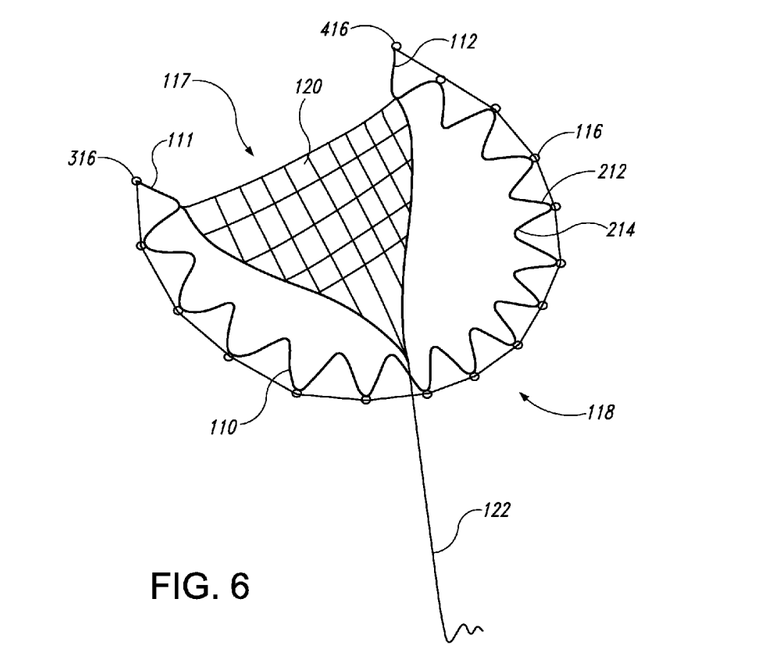
FIG. 6 is a perspective view of the body and an anterior blood-permeable member of the apparatus shown in FIG. 4.
Figure 7:
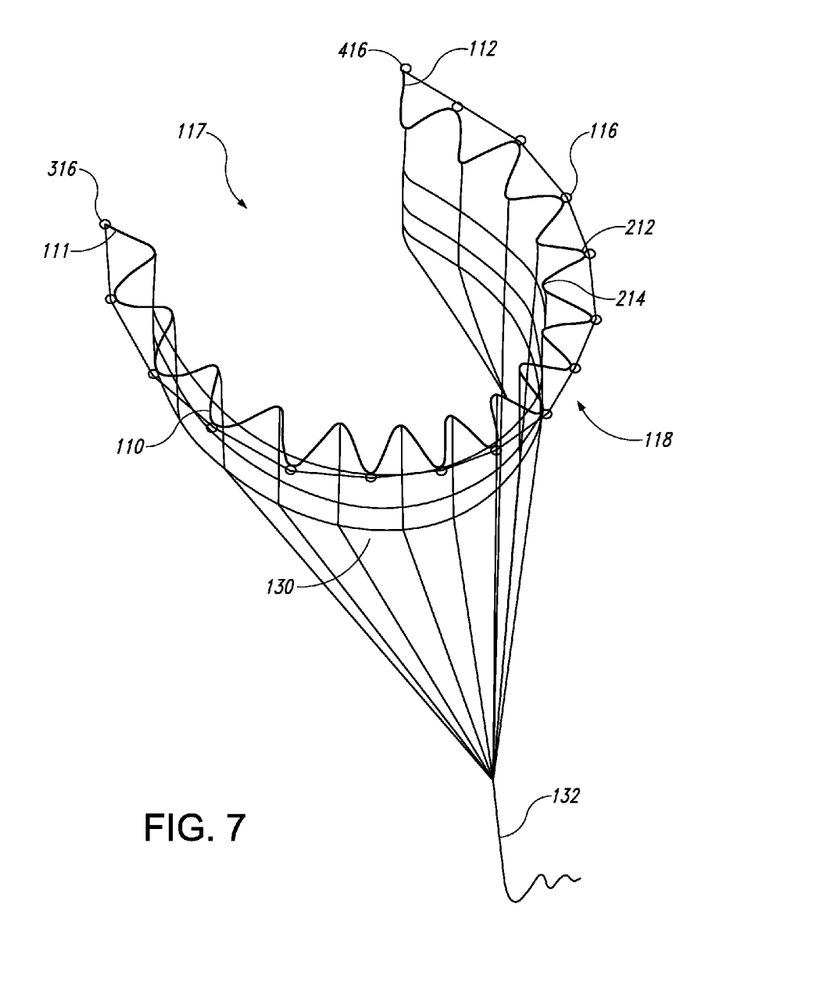
FIG. 7 is a perspective view of the body and a posterior blood-permeable member of the apparatus shown in FIG. 4.

An apparatus 100 for repairing a heart valve, such as a mitral valve, is shown in FIG. 4. Apparatus 100 includes a radially compressible and radially expandable body 110, an anterior blood-permeable member 120, and a posterior blood-permeable member 130. Although the term "radial" is most commonly used in connection with circular objects or features, it should be understood for the purpose of this description and accompanying aspects that the term "radial" is used in a broader context and is not limited to describing strictly circular objects or features or objects or features with strictly circular cross-section. Anterior blood-permeable member 120 is attached to an anterior end 117 of body 110, as shown in FIG. 6, and tapers away from body 110 terminating in an anterior cord 122. Posterior blood-permeable member 130 is attached to a posterior end 118 of body 110, as shown in FIG. 7, and tapers away from body 110 terminating in a posterior cord 132. In some embodiments, anterior blood-permeable member 120 tapers away from body 110 terminating in a plurality of anterior cords and/or posterior blood-permeable member 120 tapers away from body 110 terminating in a plurality of posterior cords. In some embodiments, anterior blood-permeable member 120 and posterior blood-permeable member 130 form a single blood-permeable member. In some other embodiments, apparatus 100 includes either anterior blood-permeable member 120 or posterior blood-permeable member 130, but not both.

Body 110 comprises a biocompatible material. In some embodiments, body 110 comprises a biocompatible metal alloy, for example nickel and/or titanium. In some embodiments, body 110 comprises Nitinol. Persons skilled in the art will recognize that body 110 may be made of other deformable and biocompatible materials conventionally used in heart surgery.

Anterior blood-permeable member 120 and posterior blood-permeable member 130 comprise a biocompatible material that permits the passage of blood therethrough. In some embodiments, anterior blood-permeable member 120 and/or posterior blood-permeable member 130 comprises one or more of polytetrafluoroethylene (PTFE), expanded PTFE, polyethylene, polypropylene, polyethylene terephthalate, and extracellular matrix biomaterial. In some embodiments, anterior blood-permeable member 120 and/or posterior blood-permeable member 130 comprises PTFE. In some embodiments, anterior blood-permeable member 120 and/or posterior blood-permeable member 130 comprises a material having tissue ingrowth qualities. Persons skilled in the art will recognize that anterior blood-permeable member 120 and posterior blood-permeable member 130 may be made of other blood-permeable, flexible, and biocompatible materials conventionally used in heart surgery.

Figures 8, 9:
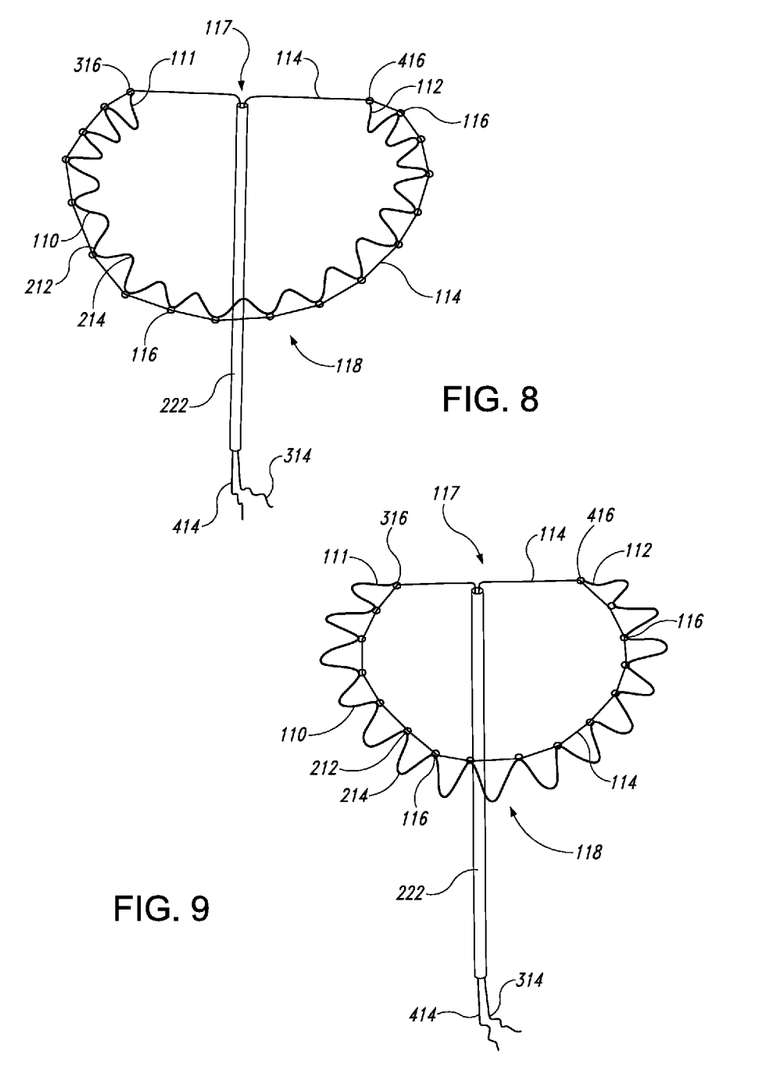
FIG. 8 is a perspective view of the body and an encircling member of the apparatus shown in FIG. 4, wherein the body is fully radially expanded and the encircling member is inserted through an encircling member sheath.
FIG. 9 is a perspective view of the body, the encircling member, and the encircling member sheath of the apparatus shown in FIG. 8, wherein the body is partially radially compressed.

In some embodiments, body 110 is C-shaped and includes a plurality of ring members 116, a plurality of peaks 212, and a plurality of troughs 214. Peaks 212 and troughs 214 are defined along the length of body 110. Ring members 116 are positioned on the plurality of peaks 212 for radially compressing and/or radially expanding body 110. In some embodiments, ring members 116 are integrally formed with body 110. In some other embodiments, ring members 116 are formed separately from body 110 and attached thereto. To radially compress and/or radially expand body 110, an encircling member 114 may be provided. A first end 314 of encircling member 114 is passed through a first ring member 316 of body 110 at first end 111 of body 110 and passes through ring members 116 along body 110 and through second ring member 416 at second end 112 of body 110. First and second ends 314, 414 of encircling member 114 extend away from body 110. By providing tension to first and second ends 314, 414 of encircling member 114, body 110 may be radially compressed. Full radial expansion of body 110 is achieved by complete tension release of encircling element 114 within ring members 116. As seen in FIG. 8, when body 110 is fully radially expanded, troughs 214 are positioned radially inwardly of peaks 212. A "purse-string" effect may be achieved when tension is applied to encircling member 114 to radially compress body 110. As seen in FIG. 9, when tension is applied to body 110 via encircling member 114 and body 110 is radially compressed, peaks 212 move radially inwardly of troughs 214. Persons skilled in the art will recognize that body 110 may be radially compressed and/or radially expanded using means conventionally known. In some embodiments, encircling element 114 is not required to radially compress and/or radially expand body 110. For example, apparatus 100 may be inserted into a heart with a balloon catheter. To position apparatus 100 inside the heart, the balloon is inflated to radially expand body 110. In some embodiments, apparatus 100 is guided into position inside the heart using one or more radio-opaque structures positioned in the coronary sinus adjacent to the posterior mitral annulus (not shown) and/or using magnets positioned in the coronary sinus (not shown).

Ring members 116 comprise a biocompatible material. In some embodiments, ring members comprise one or more of a metal, a metal alloy, PTFE, expanded PTFE, polyethylene, polypropylene, polyethylene terephthalate, and extracellular matrix biomaterial. In some embodiments, ring members 116 comprise a biocompatible metal alloy, for example nickel and/or titanium. In some embodiments, ring members 116 comprise Nitinol. Persons skilled in the art will recognize that ring members 116 may be made of other biocompatible materials conventionally used in heart surgery.

Encircling member 114 comprises a flexible and biocompatible material. In some embodiments, encircling member 114 is thread-like or wire-like. In some embodiments, encircling member 114 comprises one or more of a metal, a metal alloy, PTFE, expanded PTFE, polyethylene, polypropylene, polyethylene terephthalate, and extracellular matrix biomaterial. In some embodiments, encircling member 114 comprises a biocompatible metal alloy, for example nickel and/or titanium. In some embodiments, encircling member 114 comprises Nitinol. Persons skilled in the art will recognize that encircling member 114 may be made of other biocompatible materials conventionally used in heart surgery.

In some embodiments, body 110 includes at least one fastener 113 (FIGS. 10, 12, and 15) for securing body 110 to a left atrial wall 31 above a mitral annulus 32 of a heart (FIG. 1) when apparatus 100 is implanted in the heart. When apparatus 100 is implanted in a heart, at least one fastener 113 may face atrial wall 31 when body 110 is fully radially expanded and may face away from atrial wall 31 when body 110 is radially compressed. At least one fastener 113 comprises a biocompatible material. In some embodiments, at least one fastener 113 comprises a material having tissue ingrowth qualities. In some embodiments, at least one fastener 113 comprises at least one barb or hook.

Figure 10:
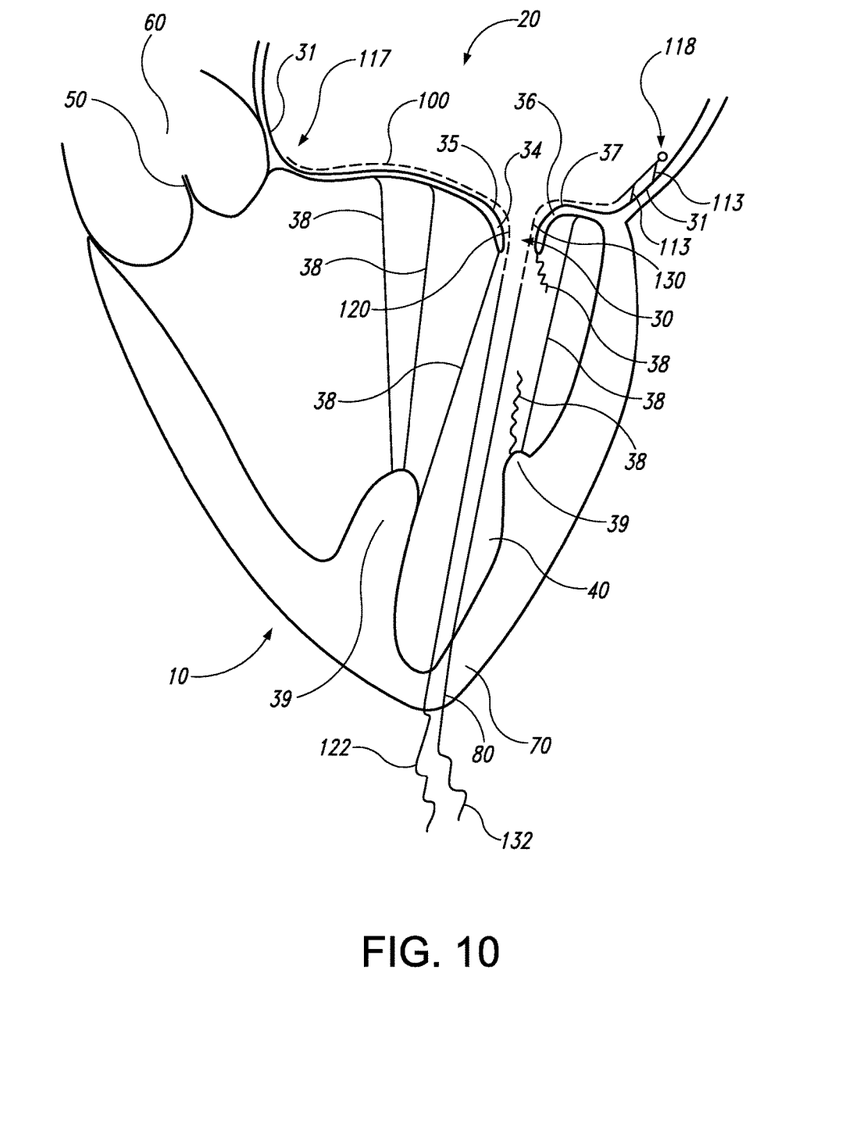
FIG. 10 is a side elevation cross-sectional view of a heart with impaired functioning of a mitral valve having an apparatus for repairing a mitral valve implanted therein.
Figure 11:
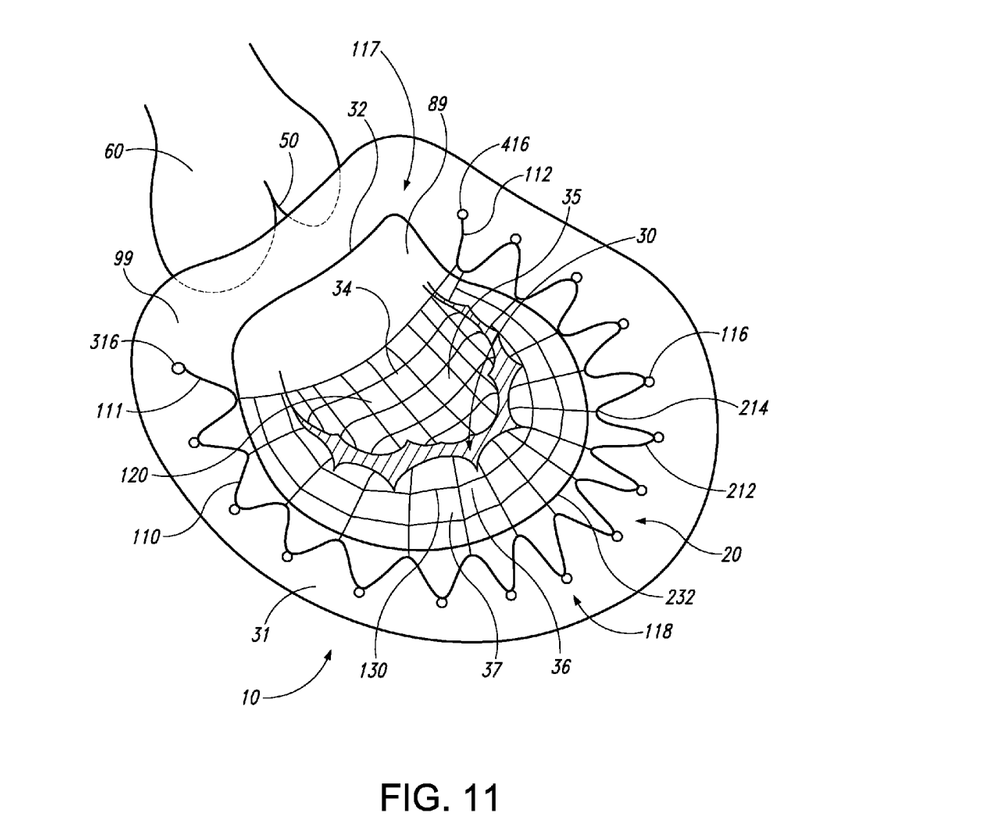
FIG. 11 is a top cross-sectional view of the heart and implanted apparatus shown in FIG. 10.

FIGS. 10 and 11 show apparatus 100 implanted in heart 10, wherein posterior blood-permeable member 130 substantially prevents atrial displacement of posterior mitral leaflet 36 despite ruptured chordae tendinae 38. Encircling member 114 has been removed from apparatus 100 and withdrawn from the heart.

As shown in FIG. 11, when apparatus 100 is implanted inside a heart, body 110 may be positioned against the atrial muscle (not shown) adjacent mitral annulus 32. For example, first end 111 of body 110 may be positioned against atrial wall 31 above lateral commissure 99, second end 112 of body 110 may be positioned against atrial wall 31 above medial commissure 89, and/or posterior end 117 of body 110 may be positioned against atrial wall 31 above posterior mitral annulus 232. In some embodiments, body 110 is shaped like the mitral annulus of a heart for positioning body 110 against the atrial muscle.

As shown in FIG. 10, anterior blood-permeable member 120 is configured to cover an atrial surface 35 of anterior mitral leaflet 34 and/or extend from left atrial wall 31 and mitral annulus 32 to a left ventricular apex 80 or a left ventricular myocardium 70 when apparatus 100 is implanted in a heart. Posterior blood-permeable member 130 is configured to cover an atrial surface 37 of posterior mitral leaflet 36 and/or extend from left atrial wall 31 and mitral annulus 32 to left ventricular apex 80 or left ventricular myocardium 70 when apparatus 100 is implanted in a heart. In some embodiments, anterior blood-permeable member 120 is sized and/or shaped like anterior mitral leaflet 34. In some embodiments, posterior blood-permeable member 130 is sized and/or shaped like posterior mitral leaflet 36.

As shown in FIG. 10, anterior cord 122 and posterior cord 132 is secured to and/or passes through left ventricular apex 80 or left ventricular myocardium 70 when apparatus 100 is implanted in a heart. By adjusting the length of anterior cord 122 and/or posterior cord 132, the extent of atrial displacement of the mitral leaflets during ventricular contraction can be adjusted. The tension of anterior cord 122 and/or posterior cord 132 may be adjusted to adjust the extent of atrial displacement of the mitral leaflets during ventricular contraction. The length and/or tension of anterior cord 122 and/or 132 may be adjusted using ultrasound guidance. When installed, apparatus 100 may correct leaflet prolapse and/or restore mitral valvular competence. In some embodiments, the length of anterior cord 122 and/or posterior cord 132 may be predetermined based on imaging measurements made before inserting apparatus 100 inside a heart.

In some embodiments, apparatus 100 includes a retaining sheath 220 for implanting apparatus 100 inside a heart (FIGS. 12 to 15). Retaining sheath 220 houses apparatus 100 for implantation. In some embodiments, retaining sheath 220 conceals at least one fastener 113 of apparatus 100 from atrial wall 31 during implantation and until apparatus 100 has been properly positioned inside the heart. To insert apparatus 100 inside retaining sheath 220, body 110 of apparatus 100 is radially compressed and apparatus 100 is then inserted inside retaining sheath 220 such that first and second ends 314, 414 of encircling member 114 extend from an end of retaining sheath 220. In some embodiments, to insert apparatus 100 inside retaining sheath 220, encircling member 114 is first inserted through ring members 116 of apparatus 110. Body 110 is then radially compressed by applying tension to encircling member 114. Radially compressed apparatus 100 is then inserted inside retaining sheath 220. Retaining sheath 220 and apparatus 100 may then be inserted into a heart to repair an abnormal mitral valve.

Figure 12:
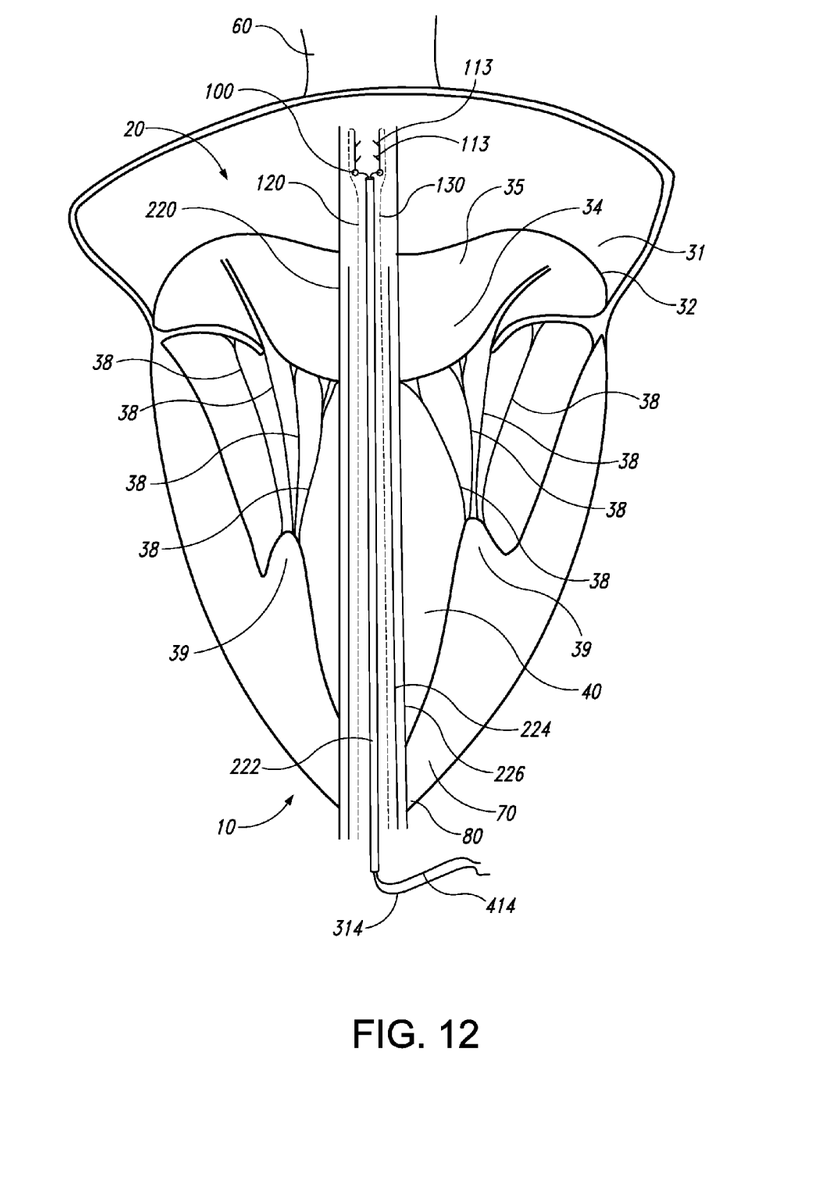
FIG. 12 is a posterior elevation cross-sectional view of a heart having an apparatus for repairing a mitral valve inserted therethrough, wherein the apparatus is retracted inside a retaining sheath.

In some embodiments, retaining sheath 220 includes an encircling member sheath 222, an inner sheath 224, and an outer sheath 226 (FIG. 12). Encircling member sheath 222, inner sheath 224, and outer sheath 226 may permit staged deployment of apparatus 100 inside a heart. First and second ends 314, 414 of encircling member 114 pass through encircling member sheath 222. Inner and outer sheaths 224, 226 house apparatus 100 and encircling member sheath 222. The dotted lines in FIG. 12 represent the anterior blood-permeable member 120 and/or posterior blood-permeable-member 130 contained alongside body 110 inside inner and outer sheaths 224, 226. Inside the heart, outer sheath 226 may be partially retracted from apparatus 100 to position body 110 of apparatus 100. Inner sheath 224 and outer sheath 224 may then be retracted from apparatus 100 to release anterior blood-permeable member 120 and/or posterior blood-permeable member 130. When apparatus 100 is properly positioned, encircling member sheath 222, inner sheath 224, and outer sheath 226 are fully retracted from apparatus 100 and withdrawn from the heart. Persons skilled in the art will recognize that some embodiments of retaining sheath 220 may include one or more of encircling member sheath 222, inner sheath 224, and outer sheath 226 for staged deployment of apparatus 100 inside a heart.

Retaining sheath 220 may comprise any material conventionally used in heart surgery that is strong enough to resist deformation that may be caused by pressure exerted on retaining sheath 220 by radially expandable body 110. In some embodiments, retaining sheath 220 comprises one or more of medical grade plastic, metal, and metal alloy. Encircling member sheath 222, inner sheath 224, and outer sheath 226 may comprise any material conventionally used in heart surgery that is strong enough to resist deformation that may be caused by pressure exerted thereon by radially expandable body 110. In some embodiments, one or more of encircling member sheath 222, inner sheath 224, outer sheath 226 comprise one or more of medical grade plastic, metal, and metal alloy.

To implant apparatus 100 inside a heart, retaining sheath 220 containing apparatus 100 is inserted through left ventricular apex 80 or left ventricular myocardium 70 into heart 10 using a transcatheter approach conventionally known. In some embodiments, retaining sheath 220 containing apparatus 100 is inserted through a ventricular septum into heart 10 using a conventionally known transcatheter approach. In some other embodiments, retaining sheath 220 containing apparatus 100 is inserted through the left atrium 20 using a transcatheter approach conventionally known.

Figure 13:
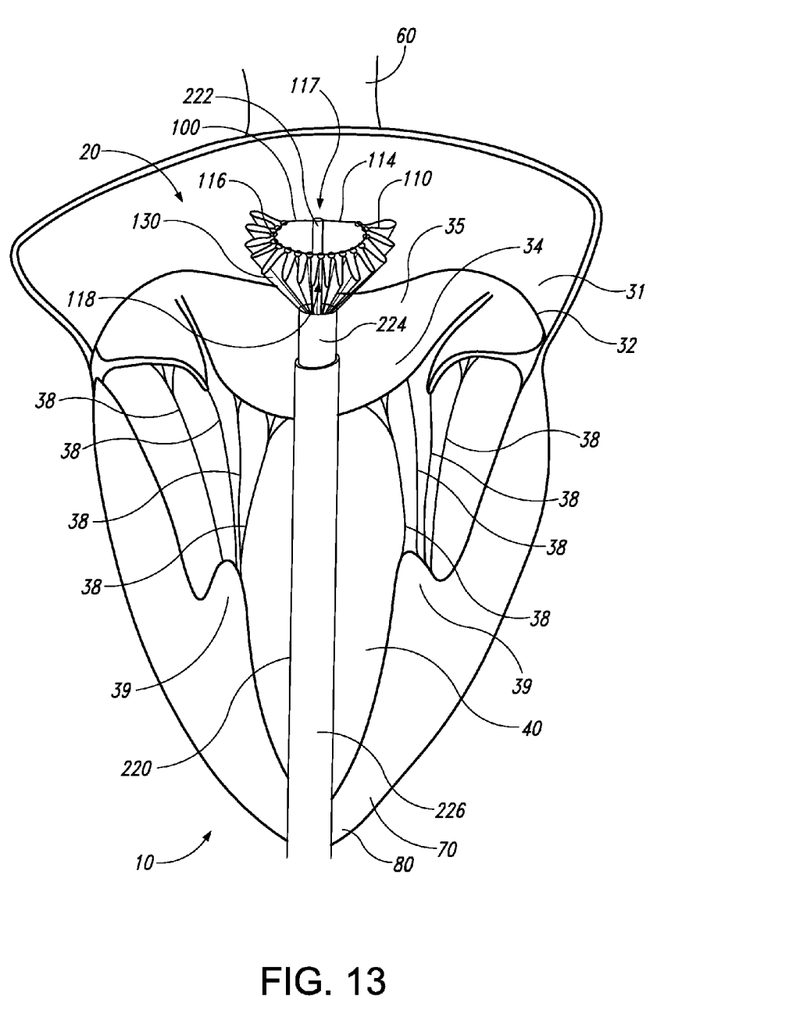
FIG. 13 is a posterior elevation cross-sectional view of the heart and apparatus shown in FIG. 12, wherein the apparatus is partially withdrawn from the retaining sheath.
Figure 14:
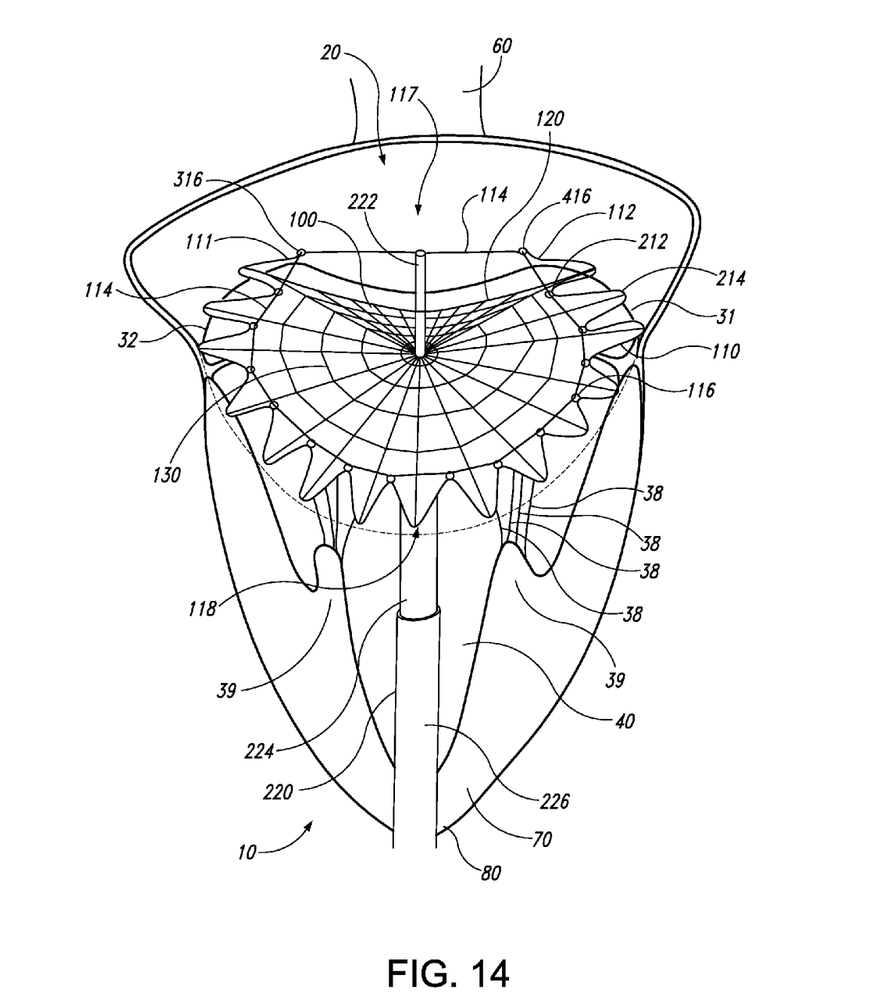
FIG. 14 is a posterior elevation cross-sectional view of the heart and apparatus shown in FIG. 12, wherein the apparatus is partially withdrawn from the retaining sheath for positioning the apparatus inside the heart.
Figure 15:
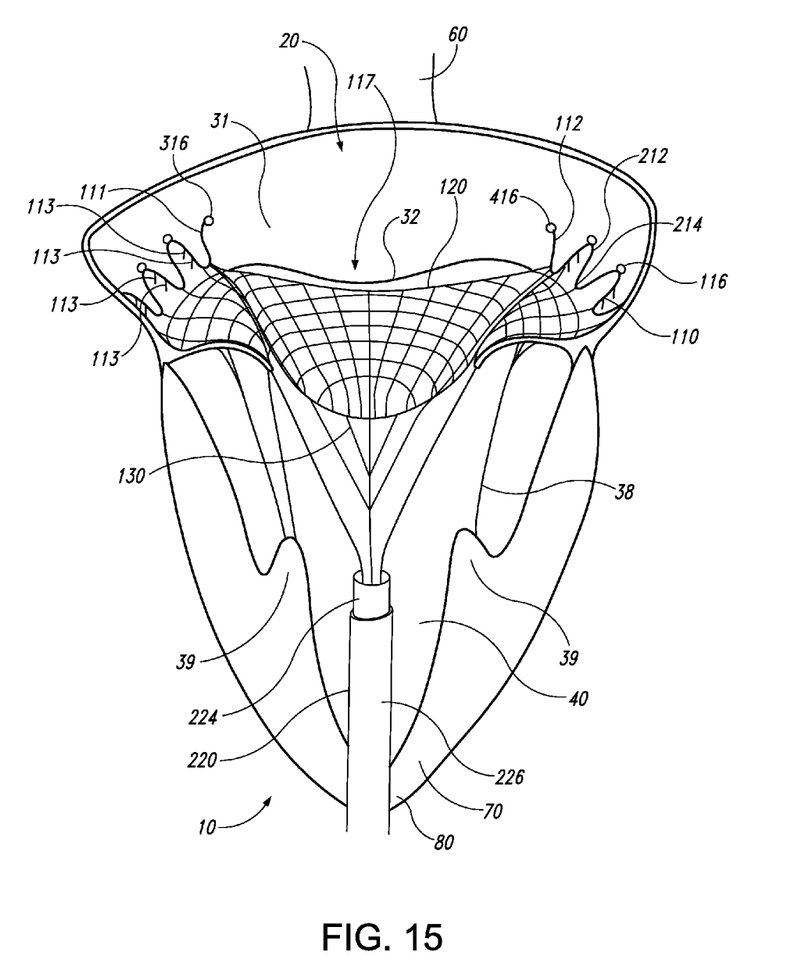
FIG. 15 is a posterior elevation cross-sectional view of the heart and apparatus shown in FIG. 12, wherein the apparatus is withdrawn from the retaining sheath and positioned inside the heart.

As shown in FIGS. 12 to 15, first and second ends 314, 414 of encircling member 114 pass through retaining sheath 220 and remain outside of the heart when retaining sheath 220 and apparatus 100 are inserted into a heart. In some embodiments, a first end of a guide wire (not shown) is inserted through left ventricular myocardium 70, across mitral valve 30, and into left atrium 20 to guide retaining sheath 220 containing apparatus 100 into the heart. In such embodiments, a second end of the guide wire (not shown) may be inserted through encircling member sheath 222. Inside the heart, outer sheath 226 may be partially retracted from apparatus 100 to release body 110 as shown in FIG. 13. Inner sheath 224 and/or encircling member sheath 222 may be partially retracted from apparatus 100 at this step. A portion of anterior blood-permeable member 120 and/or posterior blood-permeable member 130 may also be released from outer sheath 226 and/or inner sheath 224 during this step. Body 110 of apparatus 100 is rotated such that anterior end 117 of body 110 faces anterior mitral leaflet 34. Outer sheath 226 and/or inner sheath 224 is then further retracted from apparatus 100 to release anterior blood-permeable member 120 and/or posterior blood-permeable member 130 as shown in FIGS. 14 and 15. Apparatus 100 is positioned and tension is released from body 110 via encircling member 114 to cover anterior mitral leaflet 34 with anterior blood-permeable member 120 and/or cover posterior mitral leaflet 36 with posterior blood-permeable member 130. A portion of encircling member 114 may be released from encircling member sheath 222 at this step. Releasing tension in encircling member 114 allows body 110 to radially expand and contact left atrial wall 31. In some embodiments, body 110 is secured to left atrial wall 31 by one or more fasteners 113 as described elsewhere herein. If positioning of apparatus 100 is unsatisfactory, encircling element 114 may be tensioned to reposition apparatus 100. When apparatus 100 is in position, outer sheath 226 and/or inner sheath 224 is fully retracted from apparatus 100 and encircling member 114 is withdrawn from body 110. The encircling member 114 and encircling member sheath 222 may be removed from heart 10 at this step. Outer sheath 226 and/or inner sheath 224 may also be removed from heart 10 at this step. If present, the guide wire (not shown) may be removed from the heart during this step. Anterior cord 122 and/or posterior cord 132 is secured to left ventricular apex 80 or left ventricular myocardium 70 as described elsewhere herein.

INTERPRETATION OF TERMS

Unless the context clearly requires otherwise, throughout the description and the claims:
"comprise", "comprising", and the like are to be construed in an inclusive sense, as opposed to an exclusive or exhaustive sense; that is to say, in the sense of "including, but not limited to";
"connected", "coupled", or any variant thereof, means any connection or coupling, either direct or indirect, between two or more elements; the connection or coupling between the elements can be physical, logical, or a combination thereof;
"herein", "above", "below", and words of similar import, when used to describe this specification, shall refer to this specification as a whole, and not to any particular portions of this specification;
"or", in reference to a list of two or more items, covers all of the following interpretations of the word: any of the items in the list, all of the items in the list, and any combination of the items in the list;
the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Where a component (e.g. a substrate, assembly, device, manifold, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments described herein.

Specific examples of systems, methods, and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. An apparatus for repairing a heart valve, the apparatus comprising:
a radially expandable body; and
a blood-permeable member attached to the body at a first end and having at least one cord at a second end opposed to the first end,
wherein the blood-permeable member comprises a flexible material configured to permit the flow of blood from a first side of the blood-permeable member to a second side of the blood-permeable member through the blood-permeable member,
wherein the flexible material comprises one or more of polytetrafluoroethylene (PTFE), expanded PTFE, polyethylene, polypropylene, polyethylene terephthalate, and extracellular matrix biomaterial.

2. An apparatus according to claim 1, wherein the length or tension of the at least one cord is adjustable when the apparatus is implanted in a heart such that the extent of atrial displacement of the heart's mitral leaflets during ventricular contraction can be adjusted.

3. An apparatus according to claim 1, further comprising an encircling member connectable to the body for radially compressing and/or radially expanding the body.

4. An apparatus according to claim 3, wherein the body comprises a plurality of peaks and a plurality of troughs, the peaks and troughs defined along the length of the body.

5. An apparatus according to claim 4, wherein the body comprises a plurality of ring members, each ring member positioned on a corresponding peak.

6. An apparatus according to claim 5, wherein the encircling member passes through the plurality of ring members.

7. An apparatus according to claim 1, wherein the blood-permeable member comprises an anterior blood-permeable member attached to an anterior end of the body.

8. An apparatus according to claim 1, wherein the blood-permeable member comprises a posterior blood-permeable member attached to a posterior end of the body.

9. An apparatus according to claim 1, wherein the blood-permeable member is configured to extend from an atrial wall and a mitral annulus to a ventricular apex or a ventricular myocardium of the heart when the apparatus is implanted in the heart.

10. An apparatus according to claim 1, wherein the blood-permeable member is configured to cover an anterior mitral leaflet of the heart when the apparatus is implanted in the heart.

11. An apparatus according to claim 1, wherein the blood-permeable member is configured to cover a posterior mitral leaflet of the heart when the apparatus is implanted in the heart.

12. An apparatus according to claim 1, wherein the body comprises at least one fastener for securing the body to the atrial wall of the heart when the apparatus is implanted in the heart.

13. An apparatus according to claim 12, wherein the at least one fastener is positioned at one or more of a first end of the body and a second end of the body.

14. An apparatus according to claim 12, wherein each fastener comprises at least one barb or hook.

15. An apparatus according to claim 12, wherein each fastener comprises a material having tissue ingrowth qualities.

16. An apparatus according to claim 1, wherein the blood-permeable member comprises a plurality of holes that permit the flow of blood through the blood-permeable member.

17. An apparatus according to claim 1, wherein the blood-permeable member comprises at least one opening that permits the flow of blood through the blood-permeable member.

18. An apparatus according to claim 1, wherein the blood-permeable member comprises a biocompatible material.

* * * * *

UNITED STATES PATENT AND TRADEMARK OFFICE
CERTIFICATE OF CORRECTION

PATENT NO. : 10,531,956 B2
APPLICATION NO. : 15/254835
DATED : January 14, 2020
INVENTOR(S) : Peter Lloyd Skarsgard Page 1 of 1

It is certified that error appears in the above-identified patent and that said Letters Patent is hereby corrected as shown below:

On the Title Page

The (73) Assignee should be corrected as follows:
(73) Assignee: Vesalius Cardiovascular Inc., Vancouver (CA)

Signed and Sealed this
Thirteenth Day of October, 2020

Andrei Iancu
*Director of the United States Patent and Trademark Office*